United States Patent
Campochiaro et al.

(12)

(10) Patent No.: US 6,372,753 B1
(45) Date of Patent: Apr. 16, 2002

(54) METHOD OF PREVENTING PROLIFERATION OF RETINAL PIGMENT EPITHELIUM BY RETINOIC ACID RECEPTOR AGONISTS

(75) Inventors: Peter A. Campochiaro, Baltimore, MD (US); Larry A. Wheeler, Irvine, CA (US); Roshantha A. Chandraratna, Laguna Hills, CA (US); Sunil Nagpal, Lake Forest, CA (US); Eugene De Juan, Jr., Phoenix, MD (US)

(73) Assignees: Allergan, Irvine, CA (US); The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/536,221

(22) Filed: Mar. 27, 2000

Related U.S. Application Data

(63) Continuation of application No. 08/875,665, filed as application No. PCT/US96/01505 on Jan. 31, 1996, now Pat. No. 6,075,032, and a continuation-in-part of application No. 08/383,741, filed on Feb. 1, 1995, now Pat. No. 5,824,685.

(51) Int. Cl.$^7$ .................. A61K 31/435; A61K 31/07
(52) U.S. Cl. ................. 514/277; 514/725; 514/912
(58) Field of Search ................. 514/277, 725, 514/912

(56) References Cited

U.S. PATENT DOCUMENTS 5,234,926 A    8/1993   Chandraratna ............... 514/253

OTHER PUBLICATIONS

Fekrat, S., et al. "The effect of oral 13–cis–retinoic acid on retinal redetachment after surgical repair in eyes with proliferative vitreoretinopathy." Opthalmology, Mar. 1995, pp. 412–418, XP000942676.

*Primary Examiner*—Zohreh Fay
(74) *Attorney, Agent, or Firm*—Fish & Richardson P.C.

(57) ABSTRACT

Proliferation of retinal pigment epithelium following surgery or trauma or resulting in ocular diseases associated with choroidal neovascularization, such as age related macular degeneration and histoplasmosis syndrome, is prevented by contacting retinal pigment epithelium cells with a therapeutic amount of a retinoic acid receptor (RAR agonist, preferably one with specific activity for retinoic acid receptors. Preferably the RAR agonist is also a potent antagonist of AP1-dependent gene expression. Alternatively, the proliferation of retinal pigment epithelium is ameliorated with a therapeutic amount of an AP-1 antagonist, alone or in combination with an RAR agonist. The drug can be administered by bolus injection into the vitreous cavity using a dosage from about 50 to 150 μg. Or by slow release from liposomes or an oil tamponade injected into the vitreous cavity. Formulations for preventing proliferation of retinal pigment epithelium are also provided.

6 Claims, 3 Drawing Sheets

METHOD OF PREVENTING PROLIFERATION OF RETINAL PIGMENT EPITHELIUM BY RETINOIC ACID RECEPTOR AGONISTS

CROSS-REFERENCE TO RELATED APPLICATIONS

This application is a continuation of U.S. Ser. No. 08/875,665, filed Jan. 23, 1998 (U.S. Pat. No. 6,075,032, issued Jun. 13, 2000); which is a PCT National Phase application of PCT/US96/01505, filed Jan. 31, 1996, and a continuation-in-part of U.S. Ser. No. 08/383,741, filed Feb. 1, 1995 (U.S. Pat. No. 5,824,685, issued Oct. 20, 1998).

BACKGROUND OF THE INVENTION

1. Field of the Invention

This invention relates to pharmacological uses of retinoids. More particularly, this invention relates to use of retinoids in treatment of ocular disorders.

2. Description of Related Art

The retinal pigment epithelium (RPE) forms a monolayer of cells beneath the sensory retina that is normally mitotically inactive except when it is participating in retinal wound repair, in which it plays a central role. When wound repair is complete, the RPE usually stops proliferating; failure to do so can result in blinding disorders such as proliferative vitreoretinopathy (PVR) and disciform scarring. For instance, after detachment of the sensory retina, the RPE changes in morphology and begins to proliferate. Multilayered colonies of dedifferentiated RPE cells are formed. Cells then begin to migrate into the subretinal space where they engulf rod outer segments. In some instances cells migrate onto the surface of the retina and form epiretinal membranes. These events have been implicated in the pathogenesis of proliferative vitreoretinopathy, severe scarring occurring in association with macular degeneration, and poor or delayed recovery of vision after retinal reattachment.

Age-related macular degeneration (AMD) is the major cause of blindness in patients over the age of 60 in the United States. Severe loss of vision in patients with AMD is usually due to the development of choroidal neovascularization (CNV). Laser treatment can ablate CNV and help to preserve vision in selected cases not involving the center of the retina; however, the treatment benefit is often transient due to the high rate of recurrent CNV (50% over 3 years and approximately 60% at 5 years) (Macular Photocoagulation Study Group, *Arch. Ophthalmol.* 204: 694–701, 1986). In addition, many patients who develop CNV are not good candidates for laser therapy because the CNV is too large for laser treatment, or the location cannot be determined so that the physician cannot accurately aim the laser.

Despite these important consequences, little is known about the stimuli involved in RPE dedifferentiation and loss of density-dependent growth control. However, it is known that cultured human RPE rapidly become depleted of retinoids when maintained in media supplemented with fetal bovine serum (FBS) (S. R. Das, et al., *Biochem. J.*, 250:459, 1988). Retinoids have been implicated in cellular differentiation (S. Strickland, et al., *Cell,* 15:393–403, 1978; T. R. Brietman, et al., *PNAS,* 77:2936–2940, 1980; and are normally present in high levels in RPE in vivo. Retinoids play a prominent role in visual transduction and therefore their recycling is needed for normal visual function. This recycling occurs through an intimate relationship between the photoreceptors and the RPE. Disruption of this intimate relationship during retinal detachment prevents recycling of retinoids and may be one reason for outer segment degeneration and dedifferentiation of the RPE (P. A. Campochiaro, et al., *Invest. Opthalmol. Vis. Sci.,* 32:65–72, 1991).

Incubation of cultured RPE cells with all-trans retinoic acid (RA) inhibits cell proliferation and promotes a morphologic appearance like RPE in situ (P. A. Campochiaro, et al., supra; J. W. Doyle, et al., *Curr. Eye Res.* 11:753–765, 1992). All-trans RA and other derivatives of vitamin A (generally referred to as retinoids) affect the growth and differentiation of many cell types (S. Strickland, et al., supra; T. R. Breitman, et al., *Proc. Natl. Acad. Sci. USA,* 7:2936–2940, 1980). Therefore, retinoic acid or a related molecule may be one of the signals that helps to maintain or re-establish quiescence of RPE and other cells that participate in PVR.

The biological effects of retinoids are mediated through nuclear receptors which are ligand-induced trans-acting factors that bind to DNA response elements, modulating the transcription of genes containing those response elements. These receptors are divided into two major families, retinoic acid receptors (RARs) and retinoid X receptors (RXRs). For each family there are three separate gene products constituting three subtypes designated $\alpha$, $\beta$, and $\gamma$ (H. G. Stunnenberg, *Bio Essays,* 15:309–315, 1993). Alternative splicing of mRNA for these subtypes results in different isoforms and even greater diversity. The level of expression of RAR and RXR subtypes differs from tissue to tissue, and differences in activity of subtypes may provide some tissue specificity of retinoid effects (P. Dollé, et al., *Nature,* 342:702–705, 1989; J. L. Rees, et al., *Biochem. J.,* 259:917–919, 1989). Retinoid receptors up-regulate gene expression by binding to the promoter regions of RA-responsive genes as transcriptionally active RAR-RXR heterodimers (S. Nagpal, et al., *EMBO J.,* 12:2349–2360, 1993) or RXR homodimers (X. Zhang, et al., *Nature,* 358:587–591, 1992); whereas they down-regulate expression of other genes by antagonizing the effect of transcription factors such as AP-1 (M. Pfahl, *Endocrine Review,* 14:651–658, 1993; Nagpal, et al., *J. Biol. Chem* 270:923–927, 1995). AP-1 components c-Jun and c-Fos are products of immediate early genes which are produced in response to the mitogenic signals (e.g., growth factors and tumor promoters) arriving at the cell membrane. The c-Jun/c-Fos complex, in turn, activates the expression of AP-1-responsive genes involved in cell division and cell proliferation (T. Curran and B. R. Franzo, Jr., *Cell,* 55:395–397, 1988; I. R. Hart, et al., *Biochim. Biophys. Acta.* 989:65–84, 1989; P. K. Vogt and T. J. Bos, *Trends Biochem. Sci.,* 14:172–175, 1989). On the other hand, retinoids inhibit cell proliferation and induce differentiation (L. J. Guoas, et al., in *The Retinoids: Biology, Chemistry and Medicine,* eds. M. B. Sporn, et al., Raven Press Ltd., New York, pp 443–520, 1994). Therefore, in the light of the above mentioned observations, retinoid mediated antagonism of AP-1-dependent gene expression provides a basis of their anti-proliferative effects. Another level of regulation is provided by differences in ligand-receptor affinities. All trans-RA is the endogenous ligand for RARs, while that for RXRs is believed to be 9-cis-RA (R. A. Heyman, et al., *Cell,* 68:397–406, 1992; A. A. Levin, et al., *Nature,* 355:359–361, 1992); however, 9-cis-RA can bind to and activate the RARs as well. 9-cis RA is a stereoisomer of all-trans RA and is generated from all-trans RA in vivo during metabolism (R. A. Heyman, et al., supra).

Proliferative vitreoretinopathy (PVR) is the most common cause of failure following rhegmatogenous retinal detachment surgery. Despite meticulous surgical membrane removal and the use of tamponades such as silicone oil (SiO), failure occurs in a large number of cases due to difficulty with complete removal and continuous growth of the membranes. To date, the goals of surgery for PVR are to relieve traction by removal of epiretinal membranes and portions of foreshortened retina when necessary, surround all retinal breaks with retinopexy, and inject gas or silicone oil into the vitreous cavity to provide retinal tamponade for a sufficiently long period of time that all retinal breaks are sealed. Using these techniques, retinal reattachment is achieved in 35–45% of eyes with PVR with one operation, and in up to 71% of eyes with multiple operations. However, with each operation the visual prognosis worsens (Silicone Study Group, Silicone Study Report No. 2., *Arch Ophthalmol,.* 110:780–792, 1992). The major cause of failure is reproliferation with regrowth of epiretinal membranes resulting in traction and recurrent detachment. Therefore, prevention of reproliferation is a major goal in the treatment of PVR.

A number of experiments have been reported using different antiproliferative agents, such as daunomycin, alone or in combination with vitreoretinal surgery. Retinoids are lipid soluble, as most antiproliferative agents are not. All-trans RA dissolved in SiO was tested in a rabbit model of PVR, and produced a significant and lasting reduction in cellular proliferation. At doses of 2 to 20 µg/ml SiO in 3 kilogram rabbits no histological evidence of retinal toxicity was found, and the rate of retinal detachment was decreased from 100% in untreated controls to 44.5% in treated rabbit eyes at 8 weeks (J. J. Araiz, et al., *Invest. Ophthalmol. Vis. Sci.,* 34:522–30, 1993). This mode of retinoid delivery is suitable for patients with advanced PVR in whom silicone oil is often used, but is not applicable for use in patients with early or less severe PVR or those patients at high risk for PVR after retinal reattachment.

The rabbit model has also been used to test sustained delivery of RA from microspheres of biodegradable polymer in treatment of PVR (G. G. Giordano, et al., *Invest. Ophthalmol. Vis. Sci.,* 34:2743–2751, 1993). Filling the vitreous cavity with a suspension of biodegradable microspheres into which a total of about 100 µg of all-trans trans RA was incorporated significantly decreased tractional retinal detachment (TRD) in eyes treated with gas compression vitrectomy and fibroblast injection. Toxicity was limited to localized areas of inflammation felt to represent a foreign body reaction.

Retinoic acid, its geometric isomer 13-cis-retinoic acid, and synthetic derivatives have numerous biological effects in several tissues. Retinoids are currently used as the first line treatment for acute myelogenous leukemia (R. P. Warrell, Jr., et al., *N. Engl. J. Med.,* 324:1385–1393, 1991), as adjuvant therapy for several types of metastatic carcinomas (K. Dhingra, et al., *Invest. New Drugs,* 11:39–43, 1993; S. M. Lipman, et al., *J. Natl. Can. Inst.,* 85:499–500, 1993), and for treatment of psoriasis and other skin disorders. While these varied effects of retinoids provide multiple clinical applications, they are also the basis for undesired effects and toxicity that can impede the treatment of any one particular disorder. For instance, 13-cis-retinoic acid is associated with teratogenic effects when administered to pregnant females of child-bearing age. Thus, the need exists for additional synthetic retinoid analogs that avoid these toxic effects for use in treatment of PVR. Also, understanding the mechanism by which retinoids exert their antiproliferative effect in RPE cells will enable the development of new and adjunctive therapeutic agents for PVR and related diseases.

SUMMARY OF THE INVENTION

Proliferation of retinal pigment epithelium following surgery or trauma or in ocular diseases associated with choroidal neovascularization, such as age related macular degeneration and histoplasmosis syndrome, is treated by contacting retinal pigment epithelium cells with a therapeutic amount of a retinoic acid receptor (RAR) agonist, preferably one with specific activity for retinoic acid receptors and with potent ability in inhibiting AP1-dependant gene expression. This proliferation is also treated with therapeutic amounts of other agents that inhibit AP1-dependent activity, used singly or in combination with RAR agonists. The contacting can be accomplished by bolus injection into the vitreous cavity or by providing the RAR agonist in a slow release format, such as encapsulated into liposomes or dissolved in a liquid tamponade injected into the vitreous cavity or periocular space. Formulations for preventing proliferation of retinal pigment epithelium are also provided.

BRIEF DESCRIPTION OF THE DRAWINGS

FIG. 2 is a series of micrographs at magnification×150 using a phase contrast microscope showing the effect of retinoid agonists on RPE cell morphology. Magnification× 150.

FIG. 2A=serum alone; 2B=5% serum supplemented with 1 µM all-trans retinoic acid; 2C=5% serum supplemented with 1 µm of Compound 701; 2D=5% serum supplemented with 1 µm of Compound 183.

FIG. 2A=serum alone; 2B=5% serum supplemented with 1 µM all-trans retinoic acid; 2C=5% serum supplemented with 1 µm of Compound 701; 2D=5% serum supplemented with 1 µm of Compound 183.

A DETAILED DESCRIPTION OF THE INVENTION

Figure 1:
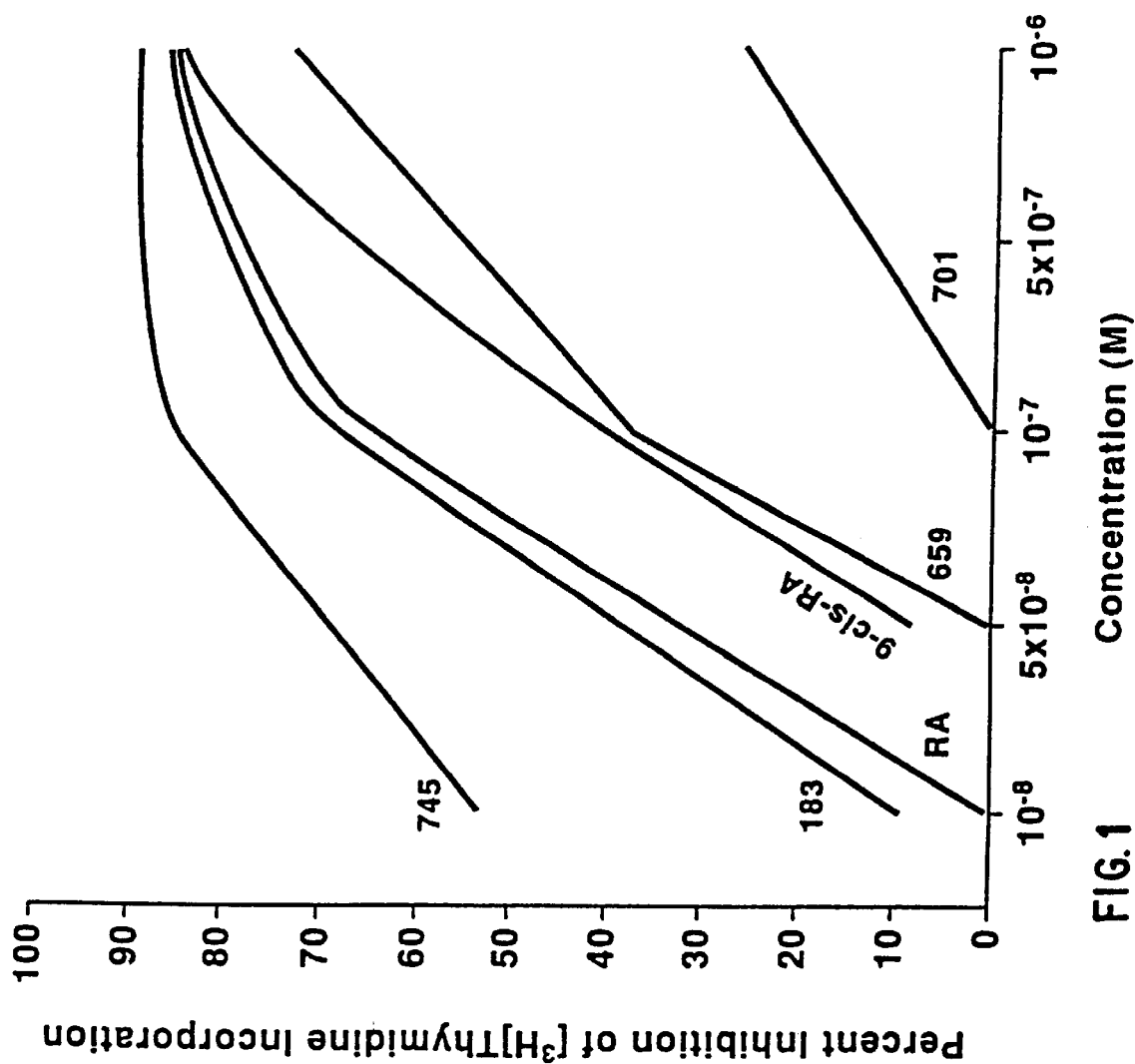
FIG. 1 is a graph showing molar concentration-dependent potency of retinoid agonists for inhibition of serum stimulated DNA synthesis in human RPE cells after incubation for 7 days. 745=Compound 745; 183=Compound 183; RA=retinoic acid; 9-cis-RA=9-cis-retinoic acid; 659=Compound 659; 701=Compound 701.

Provided herein is a method for treating proliferative vitreoretinopathy (PVR) and other disorders of retinal wound repair by contacting retinal pigmented epithelial (RPE) cells with a therapeutic amount of one or more compounds having activity as a retinoic acid receptor (RAR) agonist. It has been discovered that RAR agonists prevent the proliferation of RPE cells in vitro by promoting density arrest and a differentiated morphology in cultured RPE mediated through an RAR-activated pathway, and are also clinically effective for inhibiting traction retinal detachment in animals, such as humans, as is commonly suffered following eye surgery and other wounds to the retina that cause detachment of the RPE from the photoreceptors. These results indicate that inhibition of traction retinal detachment is mediated by a RAR-activated pathway, but not by a RXR-mediated pathway. Thus, RAR agonists are generally useful in the treatment of conditions in which there is excessive proliferation of RPE cells leading to retinal scarring or retinal detachment.

On the other hand, RXR agonists have no such useful clinical effects. Further, the primary mechanism by which RAR agonists inhibit RPE proliferation is by antagonism of AP1 activity. Thus, RAR agonists with specific anti-AP1 activity, other agents that block AP1activity, or combinations of these other agents and RAR agonists with anti-AP1 activity can be used to treat PVR.

It is shown in the Examples herein that the above-described retinoid compounds of this invention produce a differentiated phenotype in retinal epithelial cells. One of the differentiated functions of retinal pigmented epithelial cells is to prevent growth of new blood vessels from the choroid through Bruch's membrane into the space beneath the RPE, or into the subretinal space. This process is called choroidal neovascularization. It occurs in several disease processes, the most common of which is age-related macular degeneration. Consequently, treatment with the retinoid compounds of this invention helps to maintain RPE in the differentiated state and, therefore, helps to prevent choroidal neovascularization in patients.

The patients with age-related macular degeneration represent the largest group in which choroidal neovascularization is a major problem. In addition, younger patients who suffer choroidal neovascularization, such as those with ocular histoplasmosis syndrome, are also benefited by treatment with the retinoid compounds of this invention.

In the method of this invention, a therapeutically effective amount of an RAR agonist having potent activity as an antagonist of AP1 or another anti-AP1 agent or a combination of these agents is introduced into the vitreous cavity or periocular space of a patient who has PVR or choroidal neovascularization, or is at risk of developing these conditions due to disease, surgery, trauma or aging. In the case of surgery, it is particularly preferred that the RAR agonist or other anti-AP1 agent or combination be given after surgery for PVR to prevent reproliferation of RPE cells and redetachment of the retina.

As used herein, the term "a therapeutically effective amount" of an RAR agonist is an amount calculated to achieve and maintain a therapeutic level in the vitreous cavity, if introduced directly into the vitreous cavity or periocular space, or in the bloodstream, if administered peripherally over the period of time desired in a human or animal such as to substantially inhibit proliferation and thus restore differentiation of RPE. It is preferred that the therapeutic amount be an amount sufficient to inhibit proliferation of at least 50 percent, more preferably 80 percent of the RPE cells in an eye under treatment. The therapeutic amount will vary with the potency of each RAR agonist, the amount required for the desired therapeutic or other effect, the rate of elimination or breakdown of the substance by the body once it has entered the vitreous cavity or bloodstream, and the amount of the RAR agonist in the formulation. In accordance with conventional prudent formulating practices, a dosage near the lower end of the useful range of a particular agent is usually employed initially, and the dosage is increased or decreased as indicated from the observed response, as in the routine procedure of the physician.

For administration directly into the vitreous cavity of the eye, an amount in the range between about 50 and 150 $\mu$g administered within about 24 hours following surgery or trauma generally provides protection against development of PVR. In an alternative embodiment, a second dosage of the RAR agonist after an interval of several hours, usually between about 8 and 36 hours, preferably about 24 hours, is injected intravitreally or subconjunctivally. Alternatively, a combination of intravitreal and subconjunctival injection of the retinoid, either simultaneously or at the above described spaced interval, can be used to administer the retinoid. For intravitreal injection, it is preferred that the RAR agonist be injected into the anterior vitreous cavity using topical or retrobulbar anesthesia. In an alternative embodiment, the RAR agonist is introduced intravitreally using a drug delivery vehicle. For instance, the RAR agonist can be dissolved in a biologically inert fluid that is also useful as a mechanical tamponade to help keep the retina in place, preferably an oil such as silicone oil in which the retinoid is soluble. However, for RAR agonists having partial miscibility, a liquid other than an oil can be used.

However, intravitreous injection of the retinoids as a bolus injection can result in focal areas of retinal damage. In addition, it has been discovered that the therapeutic effects of the retinoids of this invention are delayed in onset and reversible. Therefore, it is advantageous to administer the retinoids utilizing a method of a slow release, for instance by intravitreal injection of the dose of retinoid encapsulated in a microvesicle, such as a liposome, from which the dose is released over the course of several days, preferably between about 3 to 20 days. Alternatively, the drug can be formulated for slow release, such as incorporation into a slow release polymer from which the dosage of drug is slowly released over the course of several days, for example from 2 to 30 days.

As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Regardless of the mode of administration, the RAR agonist can be either naturally occurring or a synthetic retinoid, preferably having selective activity as an agonist for RARs and high potency in antagonism of AP-1-dependent gene expression. Examples of naturally occurring retinoids with activity as RAR agonists are all-trans retinoic acid (all-trans RA) and 9-cis retinoic acid (9-cis RA), which are stereoisomers, all-trans RA being naturally converted into 9-cis RA during metabolism (J. G. Allen, et al., *Pharmac. Ther.*, 40:1–27, 1989). However, 9-cis RA has activity as agonists for both RARs and RXRs, and all-trans-RA, because of its metabolism or chemical isomerization to 9-cis-RA, can also effectively activate both RARs and RXRS; whereas the preferred retinoid compounds for use in the practice of this invention have specific activity as RAR agonists.

Synthetically prepared retinoids are well known in the art. For example, U.S. Pat. No. 5,234,926, which is incorporated herein by reference in its entirety, discloses methods of synthesizing disubstituted acetylenes bearing heteroaromatic and heterobicyclic groups with selective activity as RAR agonists. U.S. Pat. No. 4,326,055, which is incorporated herein by reference in its entirety, discloses methods for synthesizing 5,6,7,8-tetrahydro naphthyl and indanyl stilbene derivatives with retinoid-like activity. Since it is known that proliferation of cultured RPE cells is inhibited in vitro by retinoid compounds having activity as RAR agonists and not by compounds having activity as RXR agonists, anti-proliferative retinoid compounds can readily be selected by determining whether they have RAR activity, for instance by utilizing well known in vitro transacivation assay techniques such as that disclosed by M. Pfahl, et al., *Methods in Enzymology*, 1:256–270, 1990, and as illustrated in Example 1 of this invention. A RAR selective agonist will prevent cell overgrowth, resulting in a cell morphology indistinguishable from that caused by all-trans RA.

Examples of synthetic RAR agonists suitable for use in the practice of this invention are ethyl 6-[2-(4,4-dimethylthiochroman-6-yl)ethynyl]nicotinate (Compound 168) and 6-[2-(4,4-dimethylchroman-6-yl)ethynyl]nicotinic acid (Compound 299), whose synthesis is disclosed in U.S. Pat. No. 5,234,926 as Examples 6 and 24, respectively; and p-[(E)-2-(5,6,7,8-tetrahydro-5,5,8,8-tetramethyl-2- naphthyl)propenyl]-benzoic acid (Compound 183), whose synthesis is disclosed in U.S. Pat. No. 4,326,055. By contrast, an example of an RXR selective agonist is 2-[(E)-2-(5,6,7,8-tetrahydro-3,5,5,8,8-pentamethylnaphthaleen-2-yl)propen-1-yl]thiophene-4-carboxylic acid (Compound 701), whose synthesis is disclosed in U.S. Pat. No. 5,324,840, Example 11.

Preferably the RAR agonist is selected to be metabolically stable and to remain completely specific for the RAR pathway. Thus, all-trans RA, which isomerized to 9-cis RA during metabolism and results in activation of both the RAR and RXR pathways, is not preferred for use in the practice of this invention.

The cross-talk between the retinioid and AP-1 signal transduction pathways can be manipulated for therapeutic benefit in hyperproliferative diseases. This has been demonstrated in this invention since the retinoids that are STRONG antagonists of AP-1-dependent gene expression, are also STRONG INHIBITORS of RPE cell proliferation. Potent anti-proliferative RAR-agonists can be screened by determining their ability to inhibit AP-1-dependent gene expression in a transient transfection CAT assay as illustrated in Example 2 of this invention.

The following examples illustrate the manner in which the invention can be practiced. It is understood, however, that the examples are for the purpose of illustration and the invention is not to be regarded as limited to any of the specific materials or conditions therein.

EXAMPLE 1

The transactivation properties of retinoids were determined by measuring their ability to induce transcription in the HeLa cells by transiently cotransfecting them with a receptor gene construct and a reporter gene. Since retinoid receptors are members of the steroid receptor family of nuclear receptors that are characterized by homologous functional domains, hybrid receptors were used that contain the amino terminus and DNA-binding domain of the estrogen receptor and the hormone-binding domain of the retinoid receptors, either RAR-$\alpha$, $\beta$, $\gamma$, or RXR-$\alpha$. These ER/RAR receptors activate transcription by binding to promoter sequences recognized by the estrogen receptor (estrogen response element), but do so in response to a retinoid (D. Benbrook, et al., Nature, 333:669–672, 1988). Previous studies have shown that the activation characteristics of hybrid receptors are determined by their ligand binding domain. To determine activation of the hybrid constructs by the retinoids, an estrogen receptor-responsive reporter gene was used that cannot be activated by endogenous retinoid receptors, which are present in most, if not all, mammalian cells.

The Cationic Liposome Mediated Transfection Assay by which the activity of a test compound as a potential agonist of the RXR and RAR receptor sites is determined, is performed substantially as reported by P. L. Feigner, et al., Focus, 11:2, 1989, which is incorporated herein by reference, and is described below first in principle and thereafter in the form of specific instructions how to perform the assay.

In connection with this assay it is known that retinoic acid receptors are a member of the steroid/thyroid receptor super family and that they contain domains which are interchangeable within individual receptors. Thus, plasmids for chimeric retinoid receptors containing estrogen DNA binding domain and estrogen response element chloramphenicol acetyl-transferase (CAT) enzyme are constructed and are grown in specific cultured bacteria. These plasmids respectively code for chimeric $RAR_\alpha$, $RAR_\beta$, $RAR_\gamma$, or $RXR_\alpha$ receptor proteins, and for the chloramphenicol acetyl A transferase (CAT) enzyme protein. The bacteria with these plasmids are obtainable in accordance with the procedure set forth in the article titled "Nuclear Retinoic Acid Receptors: Cloning, Analysis, and Function", M. Pfahl, et al., Methods in Enzymology, 189: 256–270, 1990), which is incorporated herein by reference. The detailed procedure for isolating the DNA plasmids from the respective bacteria is also set forth below in detail, in the form of specific instructions under the title "Supercoiled Plasmid Isolation".

Thus, in accordance with the test procedure, a DNA plasmid that codes for one of the chimeric $RAR_\alpha$, $RAR_\beta$, $RAR_\gamma$, or $RXR_\alpha$ receptor proteins is transfected into cultures of HeLa cells. It is for this purpose that HeLa cells are grown in a medium during the first day of the assay detailed below as the "Cationic Liposome Mediated Transfection Assay". In the transfection procedure, which is performed during the second day of the transfection assay, the DNA plasmid coding for the CAT enzyme is also added to each cell culture, in addition to the respective chimeric $RAR_\alpha$, $RAR_\beta$, $RAR_\gamma$, or $RXR_\alpha$ coding plasmid.

As is known and will be readily understood by those skilled in the art, especially in view of the above-cited M. Pfahl, et al, article, chimeric retinoid receptors involved in this assay include a ligand binding domain that recognizes and binds specific agonist molecules, such as retinoic acid and analogs. These chimeric protein receptors (which were constructed in accordance with the teachings of the M. Pfahl, et al. article) also contain a DNA binding domain, which is capable of binding to the "estrogen response element" (a DNA fragment) attached to the DNA plasmid coding for the CAT enzyme. The nature of the interaction is such that only when an agonist (such as retinoic acid or analog) is bound to the ligand binding domain of the respective $RAR_\alpha$, $RAR_\beta$, $RAR_\gamma$, or $RXR_\alpha$ receptor, is the receptor bound through its DNA-binding domain to the estrogen response element of the estrogen-response-element-chloramphenicol-acetyl transferase-construct (ERE-CAT) and capable of initiating transcription of messenger RNA for the CAT enzyme. In other words, through multiple interactions CAT enzyme is manufactured by the HeLa cell in this assay only if an appropriate agonist ligand binds to the ligand binding site of the respective retinoid receptor.

The estrogen response-element-chloramphenicol acetyl-transferase construct (ERE-CAT) is itself obtained in accordance with the procedure described in G. U. Ryssel, et al. (Cell, 46:1053–1061, 1986), which is incorporated herein by reference. This procedure per se is well known in the art. The specific detailed procedure for isolating and obtaining the estrogen-response-element chloramphenicol-acetyl-transferase-construct (ERE-CAT) from bacteria is described in the procedure titled "Supercoiled Plasmid Isolation".

In addition to the foregoing, lipofectin (LF) is also added to each cell culture. The purpose of the lipofectin is to facilitate transport of plasmids through the cell membrane. The lipofectin used in the procedure is available commercially.

As will be well understood by those skilled in the art, as a result of transfection with the 25 respective DNA plasmids coding for $RAR_\alpha$, $RAR_\beta$, $RAR_\gamma$, or $RXR_\alpha$ chimeric receptors and as a result of transfection with the ERA-CAT (which codes for the CAT enzyme as described above), the aforementioned plasmids are incorporated into the HeLa cells cultured in the assay. The retinoid receptor plasmids undergo transcription (into m-RNA) and subsequent translation into the corresponding chimeric receptor protein. Therefore, the HeLa cells cultures obtained in this manner manufacture the respective $RAR_\alpha$, $RAR_\beta$, $RAR_\gamma$, or $RXR_\alpha$ chimeric receptor protein. As a result of transfection with the ERA-CAT the cell cultures of this assay also contain the genetic information for manufacturing the CAT enzyme. However, as is noted above, the latter genetic information is not transcribed, and the CAT enzyme is not manufactured by the respective cell cultures of this assay, unless an appropriate agonist compound binds to and activates the respective $RAR_\alpha$, $RAR_\beta$, $RAR_\gamma$, or $RXR_\alpha$, chimeric receptor protein in the cell and this activated agonist-receptor complex binds to the estrogen response element of the ERE-CAT construct.

The assay procedure is continued by adding, on the third day of the assay, an appropriate reference compound and the test compound (agonist or prospective agonist) to the respective HeLa cell culture, preferably in varying concentrations. As a result of this addition, if the test compound is an agonist, it binds to the respective $RAR_\alpha$, $RAR_\beta$, $RAR_\gamma$, or $RXR_\alpha$ chimeric receptor protein, and consequently the genetic information which codes for the CAT enzyme is transcribed in the cell, whereby CAT, enzyme is made by the cell.

After lysis of the cell, which is performed on the fourth day of the below-detailed assay procedure, the activity of CAT enzyme in aliquot portions of the lysate is measured. This is done by incubating the lysate with chloramphenicol and tritium labeled acetyl coenzyme A. As a final measurement, the amount of tritium labeled acetyl chloramphenicol, which is formed in the enzymatic reaction involving the CAT enzyme, is measured in a scintillation counter.

The reference compound is retinoic acid (all trans) for the assays involving the $RAR_\alpha$, $RAR_\beta$, and $RAR_\gamma$, receptors, and 4-(E)-2-(5,6,7,8-tetrahydro 3,5,5,8,8-pentamethylnaphthalen-2-yl)-propen-1-yl benzoic acid (also designated Compound 440 in this application) for the $RXR_\alpha$ chimeric receptor. The data obtained in the assay are evaluated and expressed as follows. For each test compound and for each subspecies of the RAR receptors, a graph (or the mathematical equivalent of a graph) is prepared where the "counts per minute" (cpm) obtained in the scintillation counter measurements are plotted (on the y axis) against the concentration of the test compound. A similar graph (or mathematical equivalent) is prepared for retinoic acid. EC50 of the test compound is defined as that concentration of the test compound which provides one-half (50%) of the maximum cpm number (maximum CAT enzyme activity) obtained in the same receptor in the same assay with the reference compound retinoic acid.

To evaluate and express the data obtained in the assay for the $RXR_\alpha$ the same type of graph (or mathematical-equivalent) is prepared for the test compound, and also for the reference compound, Compound 440. This reference compound is a known agonist of the $RXR_\alpha$ receptor site. $EC_{50}$ is that concentration of the test compound which gives one half (50) of the counts per minute (CAT enzyme activity) of the maximum cpm obtained with Compound 440 on the same receptor in the same assay.

SUPERCOILED PLASMID ISOLATION

Large Scale 1L Prep

DNA Isolation

1. Place cells on ice for 15 minutes. Harvest the bacterial cells (*E. coli*) by spinning down in 250 ml nalgene tubes at 7 k rpm, 10 minutes at 4° C. using JA14 rotor, Beckman J2-21 M centrifuge. Discard the supernatant.
2. To each cell pellet add 1.0 ml Solution I, vortex to resuspend the pellet. Transfer the 1.0 ml of cells from one bottle to another. Transfer this to a 50 ml Oakridge tube. Use 4 ml of Solution I and wash the bottles again transferring from one bottle to the next. Transfer this also into the Oakridge tube. Using a pipet bring up the total volume to 16 ml with Solution I and mix the solution. Transfer 8 ml to a second Oak ridge tube. Store at room temperature for 5 minutes.

Solution I 50 mM glucose, 25 mM Tris-Cl pH 8, 10 mM EDNA pH 8

3. Add to each tube ml of freshly prepared Solution II. Mix contents gently by inverting the tube several times. Store on ice for 10 minutes. After this time the liquid should be clear with no aggregates. (If there are clumps, then the cells were not resuspended well enough previously.)

Solution II

1% sodium dodecylsulfate (SDS), 0.2N NaOH (4 ml 10% SDS, 0.8 ml 10N NaOH, 35.2 ml water)

4. Add 12 ml, (or as much as will fit) of ice-cold Solution III. Mix the contents of tube by inverting it sharply several times. A white flocculent precipitate should appear. Store on ice for 10 minutes.

Solution III

Prepare as follows: to 60 ml 5M potassium acetate, add 11.5 ml of glacial acetic acid and 28.5 ml water 5. Centrifuge at 4° C. in a Beckman J2-21M centrifuge JA20 rotor, (Beckman Instruments, Carlsbad, Calif.) at 17 k rpm for 30 minutes.
6. Pipet approximately 12 ml of supernatant from the Oakridge tubes into 6 baked Corex tubes. Add 0.6 volumes of isopropanol (7.2 ml) mix by inversion and store at room temperature for 15 minutes to precipitate DNA.
7. Warm Beckman centrifuge by spinning JA20 rotor at 14 k rpm for 15 minutes at 20° C.
8. Pellet DNA at 20° C. in the J2-21M centrifuge, JA20 rotor at 10.5 k rpm for 30 minutes (use adapters for corex tubes).
9. Pour off supernatant, dry inside of tube with pasteur pipet on a vacuum flask.
10. Dry in vacuum dessicator for 10 minutes (longer drying time will make it hard to dissolve pellet).

Purify Plasmid DNA by Centrifugation to Equilibrium in CsCl Density Gradients

11. Dissolve pellet by adding 1 ml TE (10 mM Tris-Cl pH 8, 1 mM EDNA pH8) to each Corex tube. Place tubes in 37° C. water bath to help pellets to dissolve faster (15–30 minutes).
12. Transfer liquid from like batch into one tube. Bring volume to 8.5 ml with TE.
13. Add 100 μl RNase, DNase free (2 U/μl, source Boehringer Mannheim Biochemical (BMB) (Indianapolis, Ind.).
14. Add 400 μl of 10 mg/ml Ethidium Bromide.
15. Add 9.0 g CsCl and mix using a pasteur pipet.
16. Add solution to two 13×51 mm Beckman polyallomer quick-seal centrifuge tubes.
17. Spin at 50 k rpm for 12 hours in Beckman ultracentrifuge, VTi65.2 rotor, 20° C.
18. After ultracentrifugation, two bands of DNA should be visible. The upper band consists of linear bacterial DNA and nicked circular plasmid DNA. The lower band consists of closed circular plasmid DNA. Only the lower CsCl-banded DNA is removed from the tube with a 3-ml syringe fitted to an 21-gauge needle (Needle is inserted into the side of the tube and 1.5–2 ml is removed).
19. Preparation for Second CsCl centrifugation:

(9 ml–vol 1st CsCl band)–number g CsCl (9 ml–vol 1st band–100 μl 10 mg/ml Ethidium Bromide–50 μl RNase)–ml TE pH 8.0

Combine 1st band, TE, CsCl, RNase and EtBr.
20. Add solution to 2 quick-seal tubes.

21. Spin at 50 k for 12 hours or 60 k rpm for 4 hours in ultracentrifuge, VTi65.2 rotor, 20° C.
22. Remove twice CsCl-banded DNA (lower band only) to a 5 ml Falcon snap tube (as in step 18).

Extraction of Ethidium Bromide

23. Under fumehood add an equal volume isoamyl alcohol, vortex, spin at room temperature at 1500 rpm in Beckman TJ-6 centrifuge for 3 minutes.
24. Transfer bottom aqueous layer to fresh tube. Repeat 3–4 times or until aqueous layer is clear (no pink color).
25. Transfer clear aqueous layer to Spectra/Por 3 dialysis tubing, mwco 3500. (Tie a knot in the bottom of tubing before clamping dialysis tubing.) Add liquid using a pasteur pipet. Clamp top or dialysis tubing. Using a rubber band suspend tubing in 2.8 L TE (28 ml 1M Tris-Cl, pH8, 5.6 ml 0.500M EDNA, pH8). Always handle dialysis tubing carefully, with gloves.
26. Dialyze aqueous phase against several changes of 2.8 L TE pH8 (1×2–4 hours, overnight and 1×2–4 hours the next day).
27. In the tissue culture hood transfer the dialyzed DNA into sterile microcentrifuge tubes. Label tubes and store at −20° C.

Cationic Liposome-mediated Transfection

Reference: P. L. Felgner, et al., *Focus,* 11: 2, 1989.

Use Sterile Technique Throughout

Grow up HeLa or CV-1 cells in T-125 culture flask. Cells are passed twice a week, usually on Monday and Friday (0.5 ml cells into 15 ml medium).

Day 1: Plating cells

1. Trypsinize and collect cells from T-162 cm$^2$ culture flask. Count cells using a hemocytometer. Usually, this amount of cells is enough for sixteen 12-well plates.
2. Based on the cell number, dilute cells in medium (D-MEM low glucose, 10% fetal bovine serum (FBS), 2 mM 20 Glu) to a concentration of 60,000 cells per well.

Example Cell Calculation want 40,000 cells/well and 200 wells
have (X) cells/ml
therefore, 40,000 cells/well×200 wells–total # ml cells
(X) cells/ml
needed Using a 200 ml filter unit receiver add total #ml cells to medium and bring final volume to 200 ml. Mix well by pipetting.

3. Add 1.0 ml of cells per well using a sterile 12.5 ml dropper. Shake plates back and forth (do not swirl). Incubate at 37° C. in a humidified 5% CO$_2$ environment overnight. Cells are about 40% confluent prior to transfection.

Transfection: Day 2 Preparation DNA/Lipofection Complex

1. Using 50 ml polystyrene tubes prepare Lipofectin (LF) and DNA separately. Determine vol of LF and DNA needed for 2 μg LF/well, 500 ng ERE-CAT DNA/well, 100 ng ER/RAR DNA per well. Determine total volume needed for experiment. (DNA concentration will vary between each plasmid prep). Separately dilute LF and DNA in Opti-Mem media (Gibco-BRL; Gaithersburg, Md.) a volume of 25 μl×#wells: Vol Opti-Mem 1=(25 ulx#wells)−total vol. DNA or LF:

2. Add the diluted LF to the diluted DNA and swirl tube gently. Let sit at room temperature for 10 min.
3. Aspirate off the medium from the wells and wash 2× using 0.5 ml Opti-Mem I (sterile 12.5 ml combitip, setting 2).
4. Add the DNA/LF complex to vol of Opti-Mem: (450 μl×# wells). Invert tube to mix. Using a sterile 12.5 ml dropper add 500 μl to each well. Shake plates back and forth to mix, do not swirl.
5. Incubate the cells for 6 hours at 37° C. in a humidified 5% CO$_2$ incubator.
6. After 6 hours add 0.5 ml medium to each well (Dulbecco's Modified Eagle's Media (D-MEM) low glucose, 20% FBS charcoal treated, 2 mM Glu) Use 12.5 dropper and place back in the incubator.

Day 3: Drug Addition 1. 18 hours after the start of transfection add retinoids in triplicate (10 μl) using a sterile 0.5 ml dropper and incubate for 20–24 hours at 37° C. in a humidified 5% CO$_2$ environment.

Drug Dilutions weight (g)×1×100 ml=__ ml

Acetone
mol. wt (g/mol) 0.005 mol/L L

EXAMPLE

Retinoids are dissolved in acetone to a concentration of 5 mM and further diluted to 1 mM in EtOH. If retinoids do not go into solution, place tube in hot water for 5 seconds followed by vigorous vortexing. Each experiment may have a different dilution scheme. For 2 concentrations per order of magnitude use a 3.16-fold dilution as follows: To labeled sterile 12×75 mm tubes add 1080 μl of 100% EtOH. Using the 1 mM solution, transfer 500 μl to the next tube (316 μM). Vortex and repeat the transfer to the next tube down the line. Some retinoids are light sensitive, especially RA and 13-cis RA, and should be used with a red or very dim light.

EXAMPLE

| Drug Dilution 5 mM (initial) | Vol add to well | Final: −log [conc.] |
| --- | --- | --- |
| 1 mM | 10 | 5.0 |
| 316 μM | 10 | 5.5 |
| 100 μM | 10 | 6.0 |
| 31.6 μM | 10 | 6.5 |
| 10 μM | 10 | 7.0 |
| 3.16 μM | 10 | 7.5 |
| 1 μM | 10 | 8.0 |
| 316 nM | 10 | 8.5 |
| 100 nM | 10 | 9.0 |
| 31.6 nM | 10 | 9.5 |
| 10 nM | 10 | 10.0 |
| 3.16 nM | 10 | 10.5 |
| 1.0 nM | 10 | 11.0 |

Day 4 Mixed Phase Cat Assay

1. Wash cells in 12 mm wells once with 0.50 ml 1×PBS (no Ca/Mg).
2. Using a 5 ml pipet add 100 μl of a ice cold 1% Triton, 1 mM Tris-Cl pH7.8, 2 mM EDTA pH8, DNase I. Prepared as follows:

Lysis Buffer (Hypotonic Buffer)

2.0 mg DNase I (Sigma, St. Louis, Mo.)
4.925 ml water
50.0 μl 100% Triton X-100 (BMB)
5.0 μl 1M Tris-Cl pH 7.8
20.0 μl 0.5M EDTA pH 8

5.0 ml
3. Place on ice for 60 minutes. Agitate occasionally.
4. Transfer 50 μl of lysate from 3 wells at a time using titertrek multichannel pipet with tips attached to channels #1, #3, #6 to 96 U-bottom well (Costar, Cambridge, Mass.). Place (unused lysate) plates at −20° C.
5. Using a 1.25 ml combipipet (setting 1) add 50 μl premix per well, gently shake plates and incubate 37° C. for 2 hours.

| Vol. per Blank | Vol. per reaction × _____ (#assays) = total vol. |
|---|---|
| 47.0 | 27.0 μl buffer I (250 mM Tris-Cl pH 7.8, 5 mM EDTA |
| 1.5 | 1.5 μl 1 mM HCl |
| *** | 20.0 μl 5 mM Chloramphenicol (make fresh in buffer I) |
| 0.75 | 0.75 μl 4 mM Acetyl CoA in water (make fresh) |
| 0.80 | 0.80 μl 3H-Acetyl CoA (New England Nuclear, Boston, MA #NET-290L, 200 mCi/mmol |

6. Using a titertrek multichannel pipet, add 100 μl of 7M Urea (Mallincrokt, Chesterfield, Md.) into each reaction well to quench the reaction. Do six at a time.
7. Using a titertrek multichannel pipet, transfer 200 μl reaction mixture into a 5 ml plastic scintillation vial (Research Products International #125514, Mount Prospect, Ill.). Do three reactions at a time.
8. Add 1 ml 0.8% 2,5 Diphenyloxazole(PPO)/toluene (3.2 g PPO (Mallinckrodt-RPI)/4 L Toluene (Mallinckrodt ScintillAR™). Vortex vigorously for 5 seconds and allow the phases to separate for 15 minutes. Count cpm for 2.0 min-Beckman LS 3801.

The retinoid activities were determined at receptor subtypes RAR-α, RAR-β, RAR-γ and RXR-α.

Table 1 below shows the $EC_{50}$ for activation of RAR-α, β, γ, and RXR-α for each of the retinoids used in this study. Four of the agents showed good selectivity for activation of RAR receptors compared to RXR receptors. Two agents, 9-cis-RA and synthetic agonist Compound 659 activate both RAR and RXR receptors.

TABLE 1

POTENCY OF RETINOID AGONISTS AT INDUCING TRANCRIPITIONAL ACTIVATION THROUGH SPECIFIC RECEPTORS

| | $EC_{50}$ (nM) | | | |
|---|---|---|---|---|
| Compound No. | $RAR_α$ | $RAR_β$ | $RAR_γ$ | $RXR_α$ |
| 183 | 30 | 2 | 1 | 15,000 |
| 745 | 45 | 235 | 590 | N/A |
| All trans RA | 5 | 1.5 | 0.5 | >10,000 |
| 9-cis RA | 100 | 3 | 5 | 20 |
| 659 | N/A | 20 | 100 | 15 |
| 701 | N/A | 3000 | 1000 | 100 |

EXAMPLE 2

Primary cultures of human retinal pigment epithelium (RPE) cells were established from eyes obtained from the Old Dominion Eye Bank (Richmond, Va.) or the Eye Bank of Maryland (Baltimore, Md.) using the technique described in P. A. Campochiaro, et al., Invest. Ophthalmol. Vis. Sci., 27:1615–1621, 1986 which is incorporated herein by reference in its entirety.

The RPE cell lines used in this study were from two donors aged 60 and 76 years, respectively, and each was stained uniformly for cytokeratins using a known technique (K. H. Leschey, et al., Invest. Ophthalmol. Vis. Sci., 31:839–846, 1990). All-trans RA was obtained from Sigma (St. Louis, Mo.) and 9-cis retinoic acid and synthetic retinoid agonists were obtained from Allergan, Inc. (Irvine, Calif.).

For [3H]thymidine incorporation, RPE cells at passage 3 or 4 were lightly trypsinized and plated in 16-mm wells of 24-well plates. The transfected cells were allowed to attach overnight and then the media containing 5% fetal bovine serum (FBS) were supplemented with retinoids or vehicle alone. Stock solutions ($10^{-3}$M) of retinoids were prepared in dimethylsulfoxide (DMSO) and stored as frozen aliquots until used; the highest final concentration of DMSO was 0.1% and was also used for control cultures. The media containing freshly prepared retinoids were changed every three days. At 7 or 10 days 2 μCi/ml of [3H]thymidine (specific activity, 6.7 Ci/mM; New England Nuclear, Boston, Mass.) was added to the cultures and incorporation was measured as previously described (Leschey, supra).

The potency of retinoid agonists for inhibition of serum stimulated DNA synthesis in human RPE cells was tested. RPE cells ($4 \times 10^4$ cells) were plated in 16-mm wells of 24-well plates and grown for 6 days in DMEM containing 10% fetal bovine serum (Life Technologies, Inc.) supplemented with various concentrations of one of the following compounds: Compound #745, 183, 659, or 701, all-trans retinoic acid (RA) or 9-cis retinoic acid (9-cis-RA). The cells were shifted to serum-free media containing the same concentration of retinoid and then pulsed with 10% serum for 18 hours, after which [3H]thymidine incorporation was measured. Thymidine incorporation for cells grown in control medium was used to calculate the percent inhibition of thymidine incorporation induced by four concentrations of each retinoid (each concentration tested in triplicate) which were then used to generate each line.

As shown by the results summarized in FIG. 1, incubation of RPE cells for 7 days in all-trans-RA or 9-cis-RA results in dose-dependent inhibition of [3H]thymidine incorporation.

As shown by the results summarized in Table 2, a 10 day incubation results in greater inhibition and the potencies of all-trans RA and 9-cis-RA are very similar. Incubation of RPE cells for 7 or 10 days in each of four synthetic retinoids that selectively activate RAR receptors results in strong inhibition of [3H]thymidine incorporation.

TABLE 2

EFFECT OF RETINOID TREATMENT FOR TEN DAYS ON [3H] THYMIDINE INCORPORATION IN RPE CELLS

| | Percent Inhibition | | |
|---|---|---|---|
| Compound No. | $5 \times 10^{-8}$M | $10^{-7}$M | $10^{-6}$M |
| 183 | 76.7 | 98.6 | 98.8 |
| 745 | 79.2 | 98.0 | 98.6 |
| All trans RA | 52.6 | 78.3 | 99.4 |
| 9-cis RA | 57.8 | 79.8 | 98.2 |
| 659 | 20.3 | 73.2 | 38.7 |
| 701 | 12.0 | 48.8 | 74.6 |

The RXR receptor-selective agonist (Compound 701) was a much less effective inhibitor of RPE [3H]thymidine incorporation than the RAR-selective agonists, and agonists that activate both RXR and RAR receptors (9-cis RA and Compound 659) were not better inhibitors than those that activate only RAR receptors.

EXAMPLE 3

The anti-AP-1 properties of retinoids are determined by measuring their ability to inhibit AP-1-dependent gene expression in HeLa cells by transiently cotransfecting them with a reporter gene and a receptor expression vector. Since the DNA binding domain of the RARs is involved in the inhibition of AP-1-dependent gene expression (R. Schule, et al., *Proc. Natl. Acad. Sci. USA,* 88:6092–6096, 1991), holoreceptors of RARs ($\alpha$, $\beta$, USA, 88:6092–6096, 1991), holoreceptors of RARs ($\alpha$, $\beta$, and $\gamma$) are used in transfection assays to quantitate the relative potency of retinoids in antagonism of AP-1-dependent gene expression.

Recombinant Plasmids

The expression vectors for RARs ($\alpha$, $\beta$ and $\gamma$) have been described (E. A. Allegretto, et al., *J. Biol. Chem.,* 268:26625–26633, 1993). AP-1-reporter plasmid construct Str-AP-1-CAT was prepared by cloning −84 to +1 base pairs of rat stromelysin-1 promoter (L. M. Matrisian, et al., 6:1679–1686, 1986) in Hind III-Bam HI sites of pBLCAT3 (B. Luckow and G. Schutz, *Nucl. Acids Res.,* 15:5490, 1987). This sequence of stromelysin-1 promoter contains an AP-1 motif as its sole enhancer element (R. C. Nicholson, et al., *EMBO J.,* 9:4443–4454, 1990). The promoter sequence was prepared by annealing two synthetic oligonucleotides 5'-AGAAGCTT ATG GAA GCA ATT ATG AGT CAG TTT GCG GGT GAC TCT GCA AAT ACT GCC ACT CTA TAA AAG TTG GGC TCA GAA AGG TGG ACC TCG A GGATCCAG-3' (SEQ ID NO:1) AND 5'-CT GGATCC TCG AGG TCC ACC TTT CTG AGC CCA ACT TTT ATA GAG TGG CAG TAT TTG CAG AGT CAC CCG CAA ACT GAC TCA TAA TTG CTT CCA T AAGCTT CT-3' (SEQ ID NO: 2) containing Hind III and Bam HI restriction sites at their ends. The specific details for obtaining the supercoiled plasmid expression and reporter vectors have been described in detail in Example 1.

Transfection of Cells an CAT Assays

For retinoid-mediated AP-1-antagonism assay, HeLa cells grown in Dulbecco's modified Eagle's medium (DMEM), containing 10% fetal bovine serum (FBS, Life Technologies, Inc.) are transfected using the cationic liposome-mediated transfection procedure (P. L. Felgner, et al., *Focus,* 11:2, 1989). Cells are plated 18 h before transfection at about 40% confluence (40,000–50,000 cells/well) in a 12-well tissue culture plate (Costar, Cambridge, Mass.). Cells are transfected with 1 $\mu$g of reporter construct Str-AP-1-CAT and 0.2 $\mu$g of human RAR $\alpha$, $\beta$, or $\gamma$ expression vectors, along with 2 $\mu$g of Lipofectamine (Life Technologies, Inc.) for each well in a total volume of 500 $\mu$l. The details of plating of recombinant HeLa cells have been described in Example 1. DNA/Lipofectamine complexes obtained by mixing 2 $\mu$g Lipofectamine/well, 1 $\mu$g Str-AP-1-CAT/well, and 0.2 $\mu$g RAR expression vector in a 50 ml polystyrene tube are treated and incubated with HeLa cells in exactly the same manner as described for DNA/Lipofectin complexes in Example 1 of this invention. DNA is precipitated with Lipofectamine for 30 min at room temperature before transfer to cells. Five hours post-transfection, 500 $\mu$l of DMEM containing 20% charcoal treated FBS (Gemini Bioproducts, Inc., CA.) is added. All the transfections are performed in triplicate. Test retinoids (at $10^{-10}$ to $10^{-7}$ M concentrations) are added 18 h post-transfection and 6 h later the cells are treated with 12-0-tetradecanoyl phorbyl-14-acetate (TPA) to induce AP-1 activity.

Retinoids are dissolved in acetone to a concentration of 5 mM and further diluted from this stock solution using ethanol. The next day after washing with phosphate buffered saline without calcium and magnesium (Life Technologies, Inc.), the cells are harvested and lysed for 60 min with occasional agitation using a hypotonic buffer (100 $\mu$l/well) containing Dnase I, Triton X-100, Tris-HCl and EDTA as described in the mixed phase CAT assay section of Example 1 of this invention. CAT activity is assayed in 50 $\mu$l of the lysed cell extract using [$^3$H]acetyl CoA (DuPont NEN) in a 96-well U-bottom plate (Costar). The CAT activity is quantified by counting the amount of $^3$H-acetylated forms of chloramphenicol using a liquid scintillation counter. The detailed procedures of CAT assay and scintillation counting of labeled acetylated forms of chloramphenical are described in the Example 1 of this invention

TABLE 3

AP1 INHIBITION AND RPE CELL GROWTH INHIBITION

| Compound | | RPE 148 | AP1 Inhibition $EC_{50}$ (nM)[b] | | |
|---|---|---|---|---|---|
| Number | Structure | $IC_{50}$ (nM)[a] | RAR$\alpha$ | RAR$\beta$ | RAR$\gamma$ |
| All-trans RA | | <10 | 0.07 | 0.23 | <0.01 |
| 13-cis RA | | 30 | 0.08 | 10 | 1 |
| 521 | | 10 | 0.01 | 0.4 | 0.01 |
| 121 | | 30 | 0.6 | 5 | 1.9 |
| 509 | | 30 | 22 | NA | 0.01 |
| 183 | | <10 | 0.17 | <0.01 | 0.53 |
| 659 | | 10 | >$10^2$ | 14 | 22 |
| 867 | | >$10^3$ | >$10^2$ | >$10^2$ | >$10^2$ |
| 870 | | >$10^3$ | >$10^2$ | >$10^2$ | >$10^2$ |

NA = Not Available
[a]Retinoid (nM) required for 50% inhibition of RLPE cell growth relative to mock treated RPE cells.
[b]Retinoid (nM) required for 50% inhibition of Str-AP1-CAT activity in transient transfection assays.

The effects of retinoid agonists in inhibiting AP1 activity as described in Example 3 are shown in Table 3. Also shown in Table 3 are the effects of the same retinoids in inhibiting RPE cell proliferation measured as described in Example 2. Compounds that are potent inhibitors of AP1 activity (e.g., compounds 521, 183 and 659) are all effective inhibitors of RPE cell proliferation. In contrast, compounds that are ineffective inhibitors of AP1 activity (e.g., compounds 867 and 810) are also ineffective in inhibiting RPE cell proliferation.

EXAMPLE 4

Figure 3:
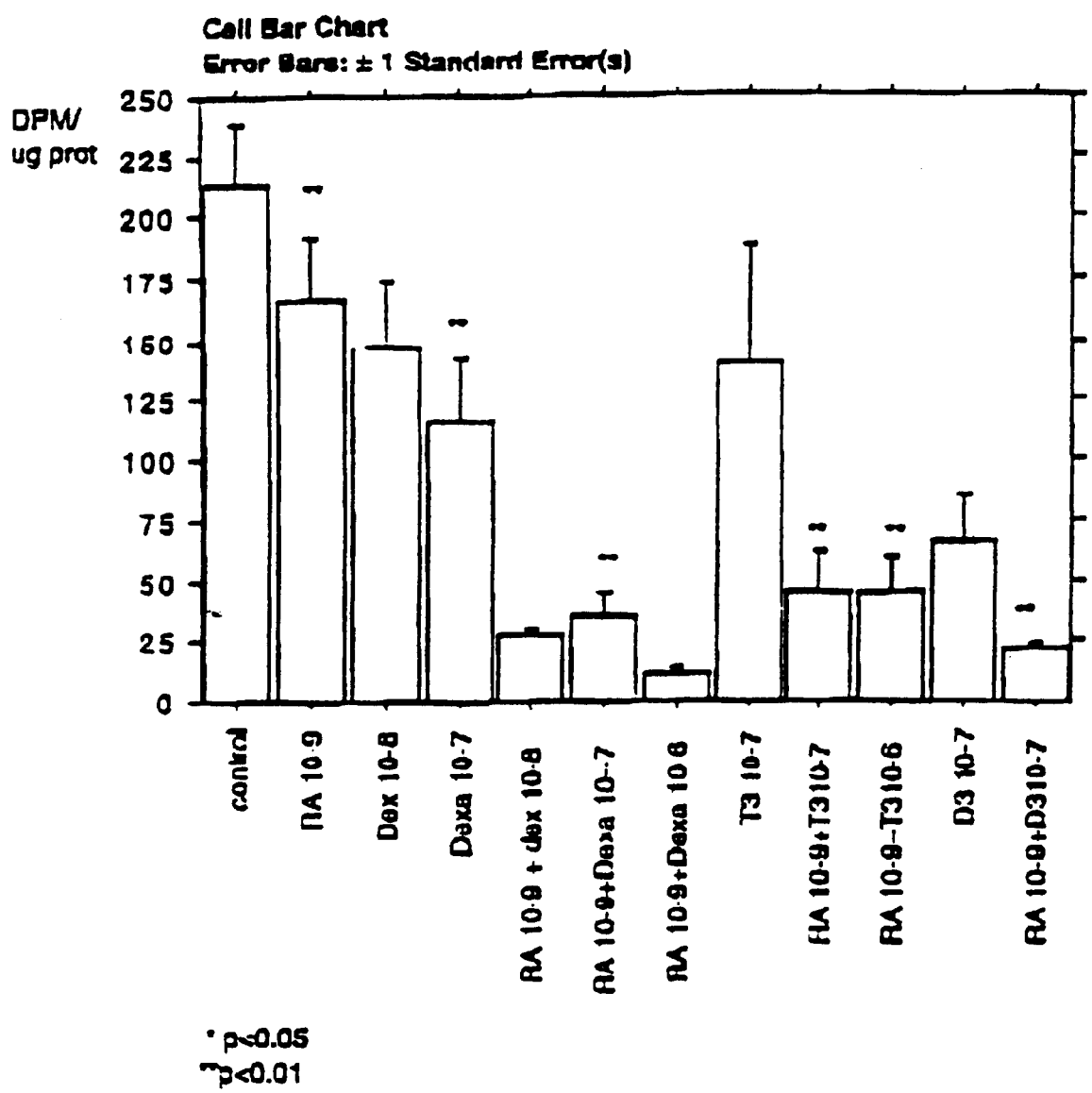
FIG. 3 is a graph showing the effect of several nuclear receptor agonists alone or in combination with retinoic acid in RPE proliferation. RA=retinoic acid; Dex and Dexa= dexamethasone; T3=thyroid hormone; D3=1,25-dihydroxyvitamin $D_3$.

Other nuclear receptors, including the thyroid hormone receptor, which is activated by thyroid hormone (T3), the is glucocorticoid receptor, which is activated by dexamethasone (Dex), and the vitamin D receptor, which is activated by 1,25-dihydroxyvitamin $D_3$ (D3), can mediate anti-AP1 activity. The effect of dexamethasone, T3 and D3 on RPE cell proliferation (measured as described in Example 2) was examined alone and in combination with retinoic acid (RA). The results are shown in FIG. 3. Dexamethasone inhibited RPE cell proliferation, but T3 and D3 did not. However, each of these agents had a synergistic effect when used in combination with retinoic acid. This provides supportive evidence that the mechanism by which RAR agonists inhibit RPE cell proliferation is by antagonism of AP1 activity and suggest that other effective inhibitors of AP1 activity, when used alone or in combination with RAR agonists, will be useful for the treatment of PVR.

EXAMPLE 5

To determine the effect of various retinoids on RPE cell morphology, RPE cells from the two donors described in Example 1 were plated in 35-mm wells and grown on plastic for 10 days in media containing 5% serum with or without one of three retinoids (1 $\mu$m); all-trans RA; a RAR selective agonist (Compound 183); or a RXR selective agonist (Compound 701).

Figure 2A:
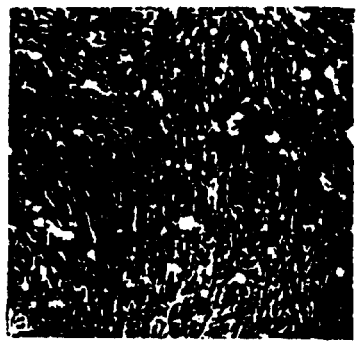
FIGS. 2A–D show cells ($4\times10^4$) from a 60 year-old donor grown in four different media.
Figure 2E:
FIGS. 2E–H show cells ($4\times10^4$) from a 76 year-old donor grown in four different media.
Figure 2B:
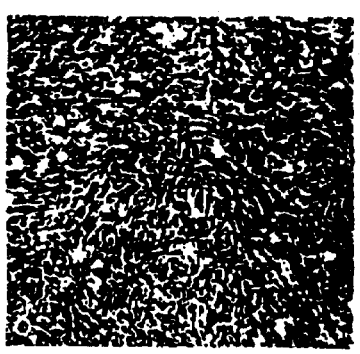
Figure 2F:
Figure 2C:
Figure 2G:
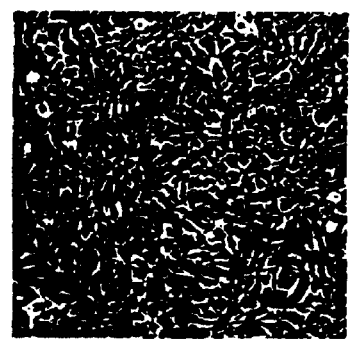
Figure 2D:
Figure 2H:
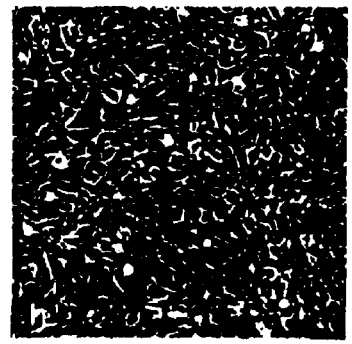

As shown in FIGS. 2A and 2B, the RPE cells grown in 5% serum containing media without other additions showed extensive overgrowth with numerous processes from one cell extending over neighboring cells. Cells treated with all-trans RA did not exhibit cell overgrowth, resulting in a morphology more like RPE in situ as shown in FIGS. 2C and 2D. The RAR selective agonist also prevented cell overgrowth, resulting in a morphology indistinguishable from that caused by all-trans RA (FIGS. 2E and 2F); whereas the RXR-selective agonist failed to prevent cell overgrowth, resulting in a morphology indistinguishable from the controls, as shown in FIGS. 2G and 2H. Trypan blue exclusion showed staining of less than 10% of cells in all cultures supplemented with each of the retinoids and was not statistically different from controls.

EXAMPLE 6

The effect of intravitreous injections of retinoids was investigated in the rabbit cell injection model of PVR first described by H. A. Sen, et al. (*Arch. Ophthalmol.*, 106:1291–1294, 1988), which is incorporated herein by reference in its entirety. Briefly, pigmented rabbits were anesthetized with a subcutaneous injection of 5 mg/kg of xylazine and 25 mg/kg of ketamine, and the pupil of one eye was dilated with 2½% phenylephrine. Under direct observation $5 \times 10^5$ RPE cells were injected into the vitreous cavity just anterior to the optic nerve. In initial experiments intravitreous injections of 100 μg of all-trans-RA, a selective RXR agonist (Compound 701), a selective RAR agonist (Compound 183), or vehicle were administered to the rabbits.

In the initial group of rabbits, five received two intravitreous injections of the RAR-selective agonist. None of these rabbits developed retinal detachments, but all experienced hair loss and loss of appetite, and two rabbits died before completion of the 28 day observation period. It was felt that the hair loss and possibly the loss of appetite and death were due to systemic toxicity from drug that had gotten out of the eye. Another group of rabbits was tested in which a single intravitreous injection of 50 μg of the RAR agonist, 50 μg and 100 μg of RA, or 100 μg of RXR agonist (701), or vehicle alone was given one day after RPE cell injection. The eyes injected with the RAR agonist or with RA had fewer (p<0.005) and less severe retinal detachments than the control eyes, but the eyes injected with the RXR agonist were not statistically different from controls. None of the rabbits experienced hair loss and none died; their appetites appeared to be normal.

EXAMPLE 7

To examine for ocular toxicity, rabbits were given a single intravitreous injection of 100 μg of all-trans-RA, the RAR-selective agonist (compound 183), the RXR-selective agonist, (compound 701), an agonist that activates both RAR and RXR (compound 659), or vehicle alone. The rabbits were killed two weeks after injection. The results of histopathologic examination of the retinas of the rabbits are

TABLE 4

EFFECT OF INTRAVITREOUS INJECTION OF RETINOIDS ON THE FREQUENCY
AND SEVERITY OF TRACTION RETINAL DETACHMENT
IN THE RABBIT CELL INJECTION MODEL OF PVR

|  |  | 14 Days | | 28 Days | | | |
| --- | --- | --- | --- | --- | --- | --- | --- |
|  | N | Partial RD | Total RD | Partial RD | Total RD | Total RD (%) | Any RD (%) |
| Vehicle Control* | 8 | 2 | 5 | 1 | 6 | 75 | 87.5 |
| Vehicle Control | 5 | 3 | 2 | 1 | 4 | 80 | 100 |
| All-trans-RA 100 μg* | 9 | 2 | 0 | 4 | 0 | 0 | 44.4+ |
| All-trans-RA 100 μg | 7 | 1 | 0 | 1 | 1 | 14.3 | 25.6+ |
| All-trans-RA 50 μg | 6 | 0 | 4 | 0 | 4 | 66.7 | 66.7 |
| RXR Agonist (Compound 701) 100 μg* | 8 | 3 | 3 | 2 | 5 | 62.5 | 87.5 |
| RXR Agonist (Compound 701) 100 μg | 5 | 2 | 2 | 1 | 3 | 60 | 80 |
| RAR Agonist (Compound 183) 100 μg* | 5 | 0 | 0 | 0 | 0 | 0 | 0++ |
| RAR Agonist (Compound 183) 50 μg | 9 | 1 | 2 | 1 | 2 | 22 | 33+ |

*Two Injections; one on day 1 after cell injection and one on day 2
+p < 0.05 for difference from control by Student's paired t-test
++p < 0.01 for difference from control by Student's paired t-test Rabbits were examined by indirect ophthalmoscopy on days 7, 14 and 28 and traction retinal detachments were graded. After injection of all trans-RA, a localized yellow cloud of precipitate appeared in the vitreous and remained for several weeks, and injection of the other agonists resulted in a while cloud. The localized clouds decreased in size and cleared over 2 to 3 weeks. There were no visible changes in the retina. As shown by the data summarized in Table 4, eyes injected with all-trans RA had fewer (p<0.05) and less severe traction retinal detachments than eyes injected with vehicle alone, while eyes injected with the RXR-selective agonist did not differ from controls.

summarized in Table 5. In general, the retinas were well-preserved and showed only mild changes believed to represent no more than artifact. As shown by the data in Table 5 below, all of the eyes, including those injected with vehicle, showed mild vitritis. One of the eyes injected with the RXR agonist and one injected with the agonist showing activity with both RXR and RAR receptors exhibited a few focal areas of retinal necrosis. The same RXR-injected eye also showed a few focal areas of inner retinal edema, and similar focal areas of inner edema were seen in one eye injected with the RAR agonist. Occasional focal areas of photoreceptor degeneration were seen in one eye injected with the RAR agonist and in one eye injected with the agonist having both RXR and RAR activity.

gated. To explore alternative methods of sustained release delivery, rabbits were given subconjunctival injections of 0.3 mg of Compound 168, 299, or RA once a day for five days after intravitreous injection of $5 \times 10^5$ human RPE cells. The results as shown in Table 7 demonstrate that, as compared with the control, subconjunctival injections of all three retinoids administered over a course of five days decreased TRD. The therapeutic effect of the RAR specific agonists was greater than that of RA, which is is an agonist for both RXRs and RARs. There were no signs of any toxicity to the retina.

TABLE 6

EFFECT OF INTRAVITREAL INJECTION OF THE RAR AGONISTS 168 AND 299 ON THE DEVELOPMENT OF TRACTION RETINAL DETACHMENT IN RABBITS AFTER INJECTION OF HUMAN RPE CELLS

| Compound | | RD at 7 Days | | RD at 14 Days | | RD at 28 Days | | % Total | % Any |
|---|---|---|---|---|---|---|---|---|---|
| No. | N | Partial | Total | Partial | Total | Partial | Total | RD | RD |
| Control | 12 | 0 | 0 | 0 | 0 | 6 | 0 | 0 | 50 |
| 168 | 12 | 1 | 0 | 1 | 0 | 7 | 1 | 8 | 80 |
| 299 | 10 | 0 | 0 | 1 | 1 | 4 | 4 | 40 | 80 |
| RA | 2 | 0 | 0 | 0 | 0 | 2 | 0 | 0 | 100 |

Areas of retinal whitening were noted in several of the drug-injected eyes, and were associated with drug

TABLE 7

EFFECT OF SUBCONJUNCTIVAL INJECTION OF THE RAR AGONISTS 168 AND 299 ON THE DEVELOPMENT OF TRACTION RETINAL DETACHMENT IN RABBITS AFTER INJECTION OF HUMAN RPE CELLS

| Compound | | RD at 7 Days | | RD at 14 Days | | RD at 28 Days | | % Total | % Any |
|---|---|---|---|---|---|---|---|---|---|
| No. | N | Partial | Total | Partial | Total | Partial | Total | RD | RD |
| Control | 12 | 0 | 0 | 0 | 0 | 6 | 0 | 0 | 50 |
| 168 | 6 | 0 | 0 | 0 | 0 | 1 | 0 | 16 | 16 |
| 299 | 4 | 0 | 0 | 0 | 0 | 0 | 0 | 0 | 0 |
| RA | 4 | 0 | 0 | 0 | 0 | 0 | 0 | 0 | 0 | precipitates, suggesting that localized areas of high concentration of Compound 168 or 299 might cause retinal damage that could be responsible for the high rate of retinal detachment. It was concluded that the poor solubility of retinoids in the vitreous resulted in precipitates and localized areas of high concentration that resulted in toxicity.

EXAMPLE 9

Due to the toxicity of certain RAR agonists and because the effects of retinoids are delayed in onset and reversible, methods for sustained release of the retinoids were investi-

EXAMPLE 10

The effect of subconjunctival injection of RAR agonists was tested in a rabbit model of PVR as described in Example 7, except that human dermal fibroblasts were injected into the vitreous cavity in the place of RPE cells. Generally, this model tends to have a higher rate of retinal detachment and more severe detachments than does the model utilizing RPE cells. However, as shown by the data in Table 8, subconjunctival injections of Compounds 168, 299, and all-trans RA all decreased the number of retinal detachments and slowed the rate at which they developed as compared with the results of the tests described in Example 9, although the improvement over the control was not as great as in Example 9.

TABLE 8

EFFECT OF SUBCONJUNCTIVAL INJECTION OF THE RAR AGONISTS 168 AND 299 ON THE DEVELOPMENT OF TRACTION RETINAL DETACHMENT IN RABBITS AFTER INJECTION OF HUMAN DERMAL FIBROBLASTS

| Compound No. | N | RD at 7 Days | | RD at 14 Days | | RD at 28 Days | | % Total RD | % Any RD |
|---|---|---|---|---|---|---|---|---|---|
| | | Partial | Total | Partial | Total | Partial | Total | | |
| Control | 10 | 2 | 0 | 5 | 0 | 7 | 1 | 10 | 80 |
| 168 | 10 | 0 | 0 | 0 | 0 | 4 | 2 | 20 | 60 |
| 299 | 10 | 0 | 0 | 0 | 0 | 4 | 0 | 0 | 40 |
| RA | 10 | 0 | 0 | 0 | 0 | 5 | 0 | 0 | 50 |

EXAMPLE 11

In this experiment the retinoid was incorporated into lipid microvesicles utilizing standard techniques. Microvesicles encapsulating all-trans RA, Compounds 168 and 299, and vehicle were injected into the vitreous cavity of rabbits on the day after intravitreous injection of $5 \times 10^5$ human dermal fibroblasts. As shown by the data in Table 9 below, microvesicles containing Compound 168 were very effective in preventing traction retinal detachment, while those containing Compound 299 or all-trans RA were not effective as compared with the control group.

TABLE 9

EFFECT OF INTRAVITREOUS INJECTION OF LIPID MICROVESICLES CONTAINING 168 OR 299 ON THE DEVELOPMENT OF TRACTION RETINAL DETACHMENT IN RABBITS AFTER INJECTION OF HUMAN DERMAL FIBROBLASTS

| Compound No. | N | RD at 7 Days | | RD at 14 Days | | RD at 28 Days | | % Total RD | % Any RD |
|---|---|---|---|---|---|---|---|---|---|
| | | Partial | Total | Partial | Total | Partial | Total | | |
| Control | 11 | 2 | 0 | 5 | 1 | 7 | 2 | 18 | 82 |
| 168 | 7 | 0 | 0 | 0 | 0 | 0 | 2 | 29 | 29 |
| 299 | 3 | 0 | 0 | 0 | 0 | 0 | 3 | 100 | 100 |
| RA | 6 | 1 | 0 | 1 | 1 | 0 | 4 | 67 | 67 |

Retinoids were incorporated into lipid microvesicles and injected subconjunctivally into the eyes of rabbits on the day after intravitreous injection of $5 \times 10^5$ human dermal fibroblasts. As shown by the data in Table 10 below, Compound 168 was substantially more effective at inhibiting tractional retinal detachment than were the other retinoids or vehicle.

TABLE 10

EFFECT OF SUBCONJUNCTIVAL INJECTION OF LIPID MICROVESICLES CONTAINING 168 OR 299 ON THE DEVELOPMEMT OF TRACTION RETINAL DETACHMENT IN RABBITS AFTER INJECTION OF HUMAN DERMAL FIBROBLASTS

| Compound No. | N | RD at 7 Days | | RD at 14 Days | | RD at 28 Days | | % Total RD | % Any RD |
|---|---|---|---|---|---|---|---|---|---|
| | | Partial | Total | Partial | Total | Partial | Total | | |
| Control | 2 | 0 | 0 | 1 | 0 | 0 | 2 | 100 | 100 |
| 168 | 8 | 0 | 0 | 1 | 0 | 0 | 2 | 33 | 33 |
| 299 | 8 | 0 | 0 | 0 | 1 | 1 | 4 | 50 | 63 |
| RA | 8 | 0 | 0 | 0 | 1 | 4 | 1 | 13 | 63 |

The foregoing description of the invention is exemplary for purposes of illustration and explanation. It should be understood that various modifications can be made without departing from the spirit and scope of the invention. Accordingly, the following claims are intended to be interpreted to embrace all such modifications.

SUMMARY OF SEQUENCES

SEQ ID NO: 1 is an oligonucleotide primer for the stromelysin-1 promoter.
SEQ ID NO: 2 is an oligonucleotide primer for the stromelysin-1 promoter.

What is claimed is:

1. A method for inhibition of an ocular disease resulting from proliferation of retinal pigment epithelium (PRE) comprising contacting the retinal pigment epithelial cells of a patient in need thereof with a therapeutic amount of at least one AP-1 antagonist and at least one retinoic acid receptor (RAR) agonist, except for retinoic acid.

2. A method of inhibition of a hyperproliferative ocular disease comprising contacting the retinal pigment epithelial cells of a patient in need thereof with a therapeutic amount of at least one AP-1 antagonist and at least one retinoic acid receptor agonist, except for retinoic acid.

3. A method for inhibition of an ocular disease resulting from choroidal neovascularization (CNV) comprising contacting the retinal pigment epithelial cells of a patient in need thereof with a therapeutic amount of at least one AP-1 antagonist.

4. The method of claim 3 wherein the AP-1 antagonist is administered in combination with at least one retinoic acid receptor agonist, except for retinoic acid.

5. A method for screening anti-proliferative RAR agonists comprising determination of their ability to inhibit AP-1-dependent gene expression.

6. The method of claim 5 wherein the AP-1-dependent gene expression inhibition ability is determined in a transient transfection CAT assay.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 101 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..101

(xi) SEQUENCE DESCRIPTION: SEQ ID NO:1:

```
AGAAGCTTAT GGAAGCAATT ATGAGTCAGT TTGCGGGTGA CTCTGCAAAT A CTGCCACTC        60

TATAAAAGTT GGGCTCAGAA AGGTGGACCT CGAGGATCCA G                           101
```

(2) INFORMATION FOR SEQ ID NO:2:

(i) SEQUENCE CHARACTERISTICS:
      (A) LENGTH: 101 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..101

(xi) SEQUENCE DESCRIPTION: SEQ ID NO:2:

```
CTGGATCCTC GAGGTCCACC TTTCTGAGCC CAACTTTTAT AGAGTGGCAG T ATTTGCAGA        60

GTCACCCGCA AACTGACTCA TAATTGCTTC CATAAGCTTC T                           101
```